(12) United States Patent
Huang et al.

(10) Patent No.: US 11,691,965 B2
(45) Date of Patent: Jul. 4, 2023

(54) METHOD FOR PREPARING PYRROLIDINYL UREA DERIVATIVE

(71) Applicant: ZHANGZHOU PIEN TZE HUANG PHARMACEUTICAL CO., LTD., Fujian (CN)

(72) Inventors: Jinming Huang, Zhangzhou (CN); Juan Yu, Zhangzhou (CN); Jinxiang Zeng, Zhangzhou (CN); Limei Yang, Zhangzhou (CN); Tingting Yin, Zhangzhou (CN); Yang Zhang, Shanghai (CN); Wentao Wu, Shanghai (CN); Zhixiang Li, Shanghai (CN); Jian Qin, Shanghai (CN)

(73) Assignee: ZHANGZHOU PIEN TZE HUANG PHARMACEUTICAL CO., LTD., Fujian (CN)

( * ) Notice: Subject to any disclaimer, the term of this patent is extended or adjusted under 35 U.S.C. 154(b) by 0 days.

(21) Appl. No.: 17/791,626

(22) PCT Filed: Jan. 8, 2021

(86) PCT No.: PCT/CN2021/070962
§ 371 (c)(1),
(2) Date: Jul. 8, 2022

(87) PCT Pub. No.: WO2021/139795
PCT Pub. Date: Jul. 15, 2021

(65) Prior Publication Data
US 2023/0065496 A1 Mar. 2, 2023

(30) Foreign Application Priority Data
Jan. 10, 2020 (CN) .......................... 202010027384.1

(51) Int. Cl.
*C07D 405/14* (2006.01)
(52) U.S. Cl.
CPC ................. *C07D 405/14* (2013.01)
(58) Field of Classification Search
CPC ................................................. C07D 405/14
USPC ........................................................ 544/333
See application file for complete search history.

(56) References Cited

U.S. PATENT DOCUMENTS

| | | |
|---|---|---|
| 2017/0240512 A1 | 8/2017 | Yukimasa et al. |
| 2018/0201607 A1 | 7/2018 | Yukimasa et al. |
| 2019/0047998 A1 | 2/2019 | Yukimasa et al. |
| 2019/0359597 A1 | 11/2019 | Allen et al. |
| 2021/0147436 A1 | 5/2021 | Zhang et al. |

FOREIGN PATENT DOCUMENTS

| | | |
|---|---|---|
| CN | 103649076 A | 3/2014 |
| WO | 2012158413 A2 | 11/2012 |
| WO | 2015175788 A1 | 11/2015 |
| WO | 2016021629 A1 | 2/2016 |
| WO | 2016116900 A1 | 7/2016 |
| WO | 2017006953 A1 | 1/2017 |
| WO | 2020011227 A1 | 1/2020 |

OTHER PUBLICATIONS

International Search Report (English and Chinese) issued in PCT/CN2021/070962, dated Apr. 16, 2021; ISA/CN.
Written Opinion of the International Searching Authority (English and Chinese) issued in PCT/CN2021/070962, dated Apr. 16, 2021; ISA/CN.
CN2020100273841, filed Jan. 10, 2020, as priority claimed in International Patent Application No. PCT/CN2021/070962.

*Primary Examiner* — Kahsay Habte
(74) *Attorney, Agent, or Firm* — Harness, Dickey & Pierce, P.L.C.

(57) ABSTRACT

Disclosed is a method for preparing a pyrrolidinyl urea derivative, which acts as a TrkA inhibitor, and further disclosed are an intermediate compound of a compound of formula (I) and a preparation method therefor.

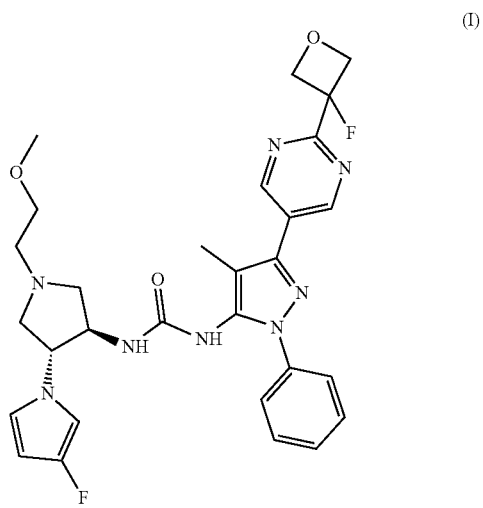

20 Claims, No Drawings

METHOD FOR PREPARING PYRROLIDINYL UREA DERIVATIVE

CROSS-REFERENCE TO RELATED APPLICATIONS

This application is a U.S. National Phase Application under 35 U.S.C. 371 of International Application No. PCT/CN2021/070962, filed on Jan. 8, 2021, which claims the benefit of Chinese Patent Application No. 202010027384.1, filed on Jan. 10, 2020. The entire disclosures of the above applications are incorporated herein by reference.

TECHNICAL FIELD

The present disclosure relates to a method for preparing a pyrrolidinyl urea derivative as a TrkA inhibitor, and also relates to an intermediate compound of compound represented by formula (I) and a preparation method thereof.

BACKGROUND

Tropomyosin-related kinase (Trk) is a high-affinity receptor tyrosine kinase activated by a group of soluble growth factors called nerve growth factor (NGF), brain-derived neurotrophic factor (BDNF), neurotrophic factor (NT), whose family consists of three members (TrkA, TrkB, TrkC). NGF, BDNF and NT-4/5 play an important role in many physiological regulation processes such as signal maintenance, signal transmission, cell proliferation, cell differentiation and cell survival of neuronal cells through receptor Trk. There is a lot of evidence that inhibitors of the NGF/Trk signaling pathway are effective in many preclinical models of pain; inhibitors of the NGF/Trk signaling pathway have also been shown to be effective in many preclinical models of inflammatory diseases. Furthermore, overexpression, activation, amplification and/or mutation of Trk kinase are associated with many tumors or cancers. Therefore, Trk has emerged as an important class of therapeutic target, attracting extensive research and development interest. The TrkA inhibitors of the present disclosure can solve the treatment needs of pain, cancer, inflammation, neurodegenerative diseases and certain infectious diseases.

WO2015175788 patent reported a single compound with inhibitory activity against TrkA and a pharmaceutically acceptable salt thereof. WO2012158413, WO2016116900, WO2016021629 and WO2017006953 have reported a series of compounds with inhibitory activity against TrkA, including the pyrrolidinyl urea structure used in the present disclosure.

CONTENT OF THE PRESENT INVENTION

The present disclosure provides a method for preparing compound represented by formula (I),

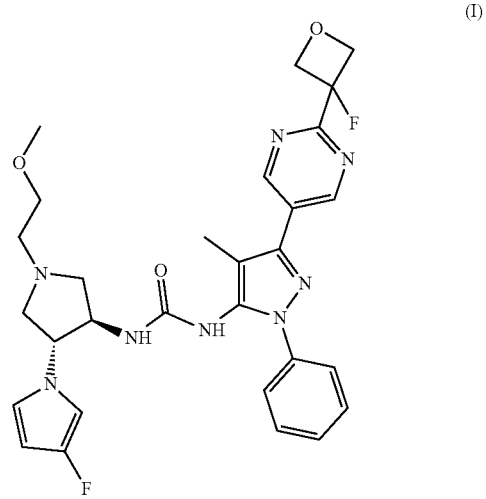 [SMILES: COCCN1C[C@@H](n2ccc(F)c2)[C@H](NC(=O)Nc2c(C)c(-c3cnc(C4(F)COC4)nc3)nn2-c2ccccc2)C1]

comprising the following steps:

step 1: reacting compound represented by formula SM3-9 with compound represented by formula SM3-10 to obtain compound represented by formula SM3-11,

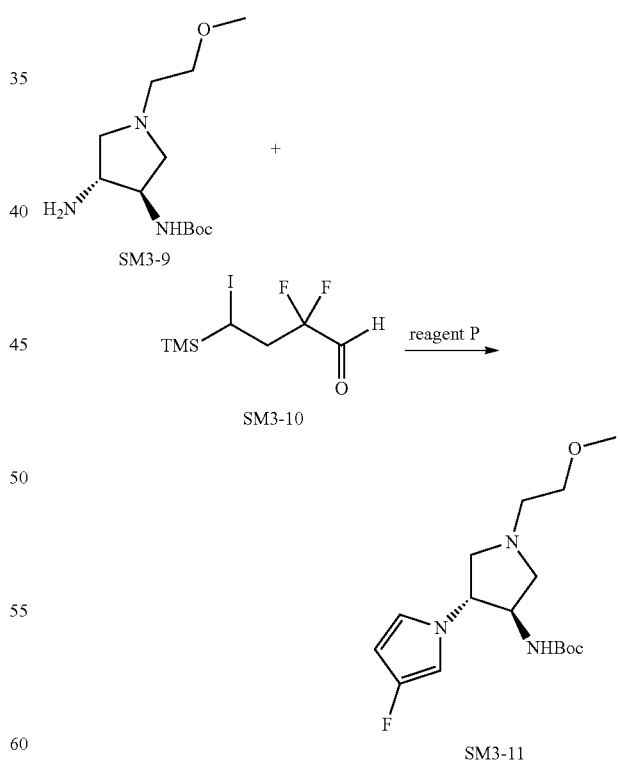

step 2: reacting compound represented by formula SM1 with compound represented by 1-1 to obtain an intermediate compound, which is reacted with compound represented by formula SM2 to obtain compound represented by formula 1-2,

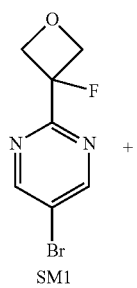

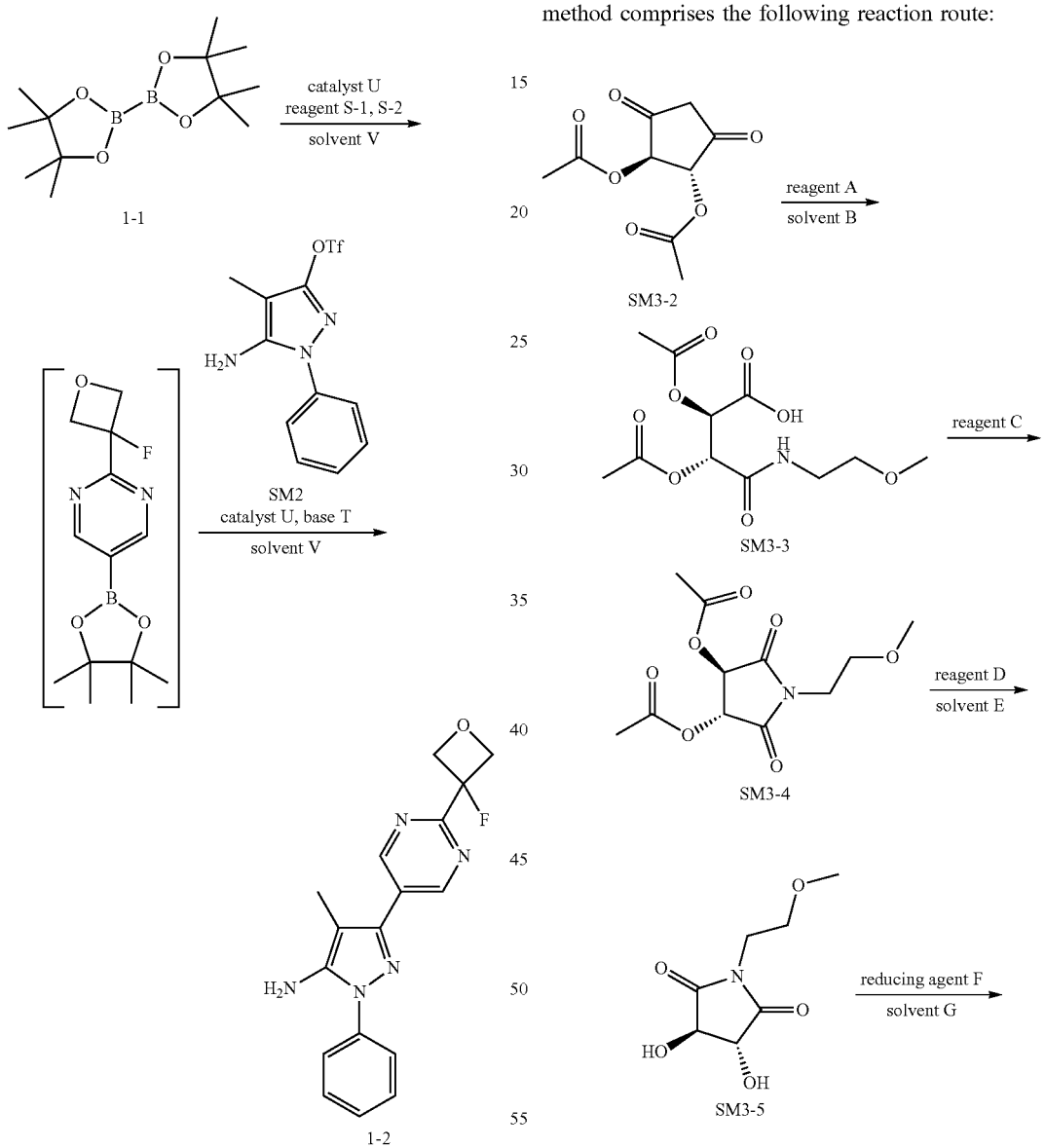

catalyst U is selected from palladium acetate, (diphenylphosphino)ferrocene dichloropalladium(II), tetrakis(triphenylphosphine)palladium, allylpalladium(II) chloride dimer, di-μ-chlorobis[(1,2,3-η)-1-phenyl-2-propenyl]dipalladium(II) and palladium trifluoroacetate;

base T is selected from sodium carbonate, cesium carbonate and potassium carbonate;

solvent V is selected from dioxane, methylcyclopentyl ether, toluene, methyltetrahydrofuran and tetrahydrofuran.

In some embodiments of the present disclosure, the method comprises the following reaction route:

wherein, reagent P is acetonitrile;

reagent S-1 is potassium acetate;

reagent S-2 is selected from tricyclohexylphosphine, 2-di-tert-butylphosphino-3,4,5,6-tetramethyl-2',4',6'-triisopropyl-1,1-biphenyl, 2-(dicyclohexylphosphino)-3,6-dimethoxy-2-4-6-triisopropyl-1,1-biphenyl, triphenylphosphine and 2-dicyclohexylphosphino-2,4,6-triisopropylbiphenyl;

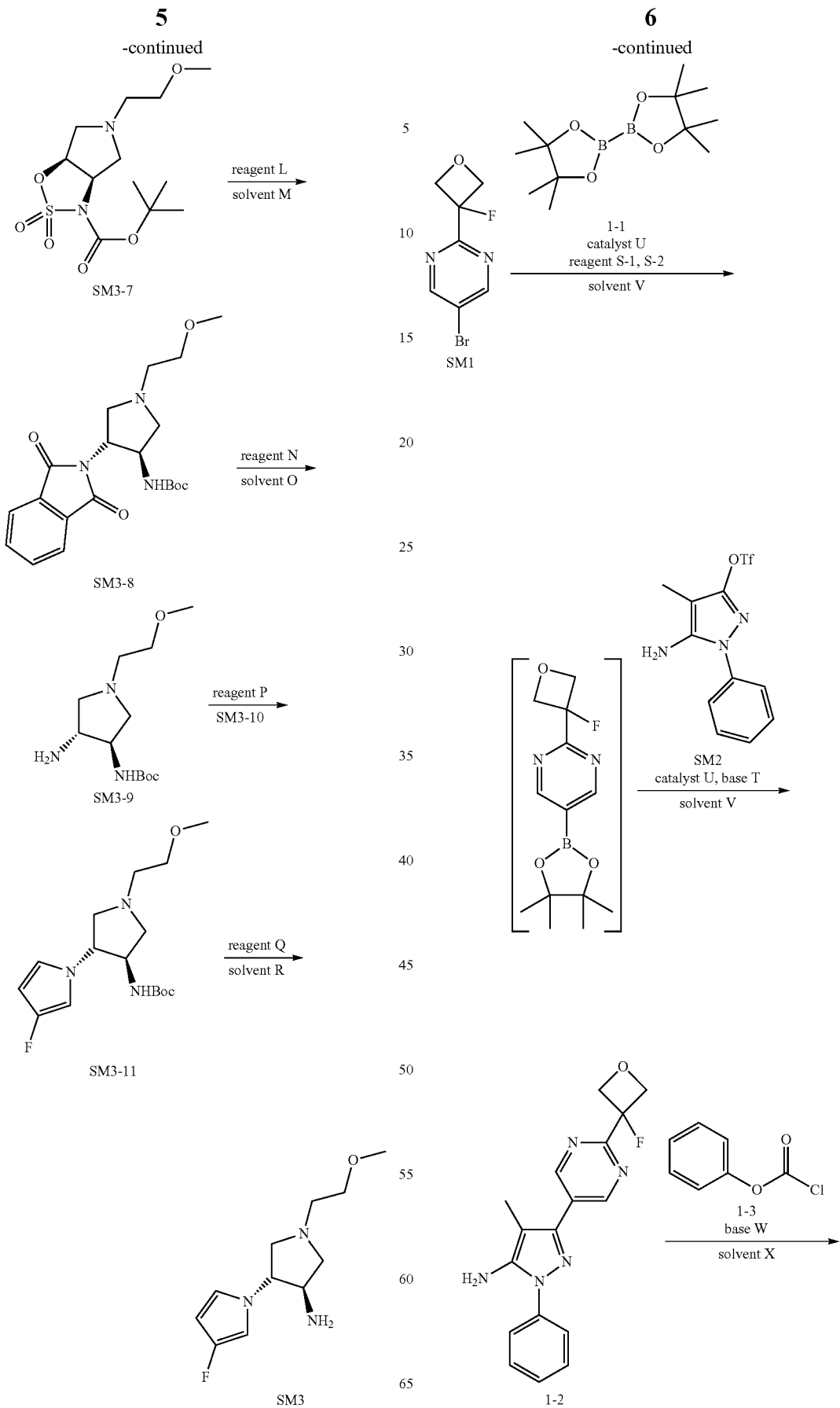

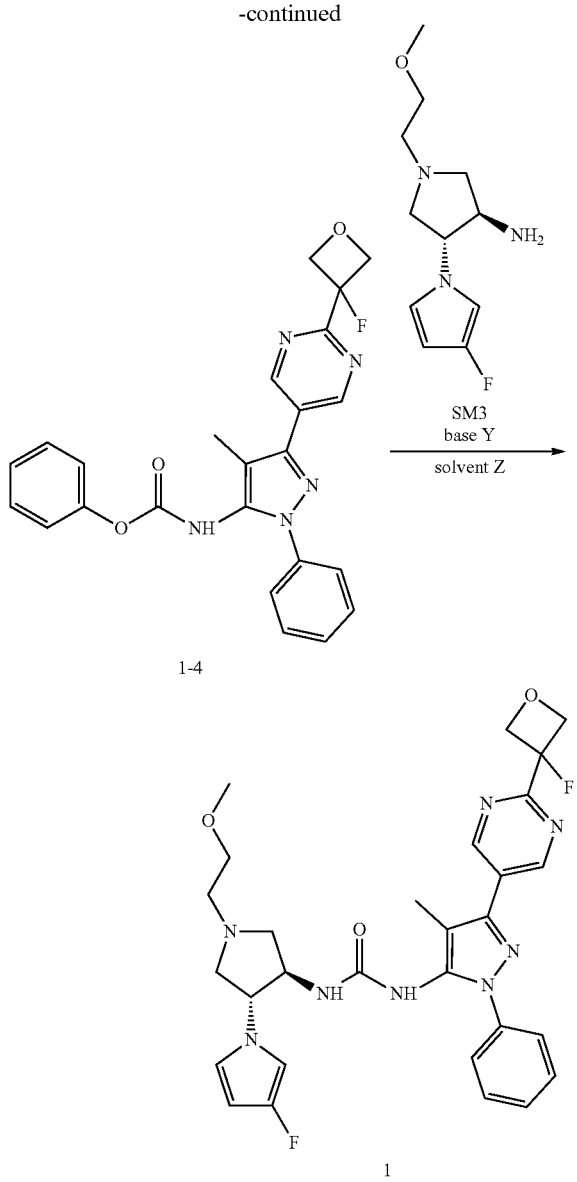

wherein,
reagent A is 2-methoxyethylamine;
solvent B is tetrahydrofuran;
reagent C is acetyl chloride;
reagent D is acetyl chloride;
solvent E is ethanol;
reducing agent F is selected from lithium aluminum hydride (flake), borane tetrahydrofuran solution and borane dimethyl sulfide complex;
solvent G is tetrahydrofuran;
reagent H is sulfonic acid isocyanate;
reagent I is tert-butanol;
base J is selected from triethylamine and diisopropylethylamine;
solvent K is selected from dioxane and dichloromethane;
reagent L is selected from phthaloyl potassium salt, sodium hydride, potassium tert-butoxide, sodium tert-butoxide, potassium carbonate and 1,8-diazabicyclo[5.4.0]undec-7-ene/phthalamide;
solvent M is selected from N,N-dimethylformamide, tetrahydrofuran, methanol, dioxane and dimethyl sulfoxide;

reagent N is hydrazine hydrate;
solvent O is ethanol;
reagent Q is selected from p-toluenesulfonic acid, hydrochloric acid and trifluoroacetic acid;
solvent R is selected from tetrahydrofuran, dichloromethane and ethyl acetate;
base W is selected from pyridine, triethylamine, diisopropylethylamine and sodium bicarbonate;
solvent X is selected from dichloromethane, N,N-dimethylformamide, tetrahydrofuran and ethyl acetate;
base Y is selected from sodium carbonate, diisopropylethylamine, triethylamine, pyridine, sodium bicarbonate, potassium carbonate and sodium hydroxide;
solvent Z is selected from tetrahydrofuran/water, methyltetrahydrofuran, dichloromethane and methyltetrahydrofuran/water.

In some embodiments of the present disclosure, in the method, wherein, in the step of preparing compound SM3-11, the temperature range of the reaction system is controlled to be 65±5° C.

In some embodiments of the present disclosure, in the method, wherein, the molar ratio of compound SM3-9 to compound SM3-10 is 1:1.2 to 2.

In some embodiments of the present disclosure, in the method, wherein, the molar ratio of compound SM1 to catalyst U is 1:0.05 to 0.1.

In some embodiments of the present disclosure, in the method, wherein, in the step of preparing compound SM3-3, when adding the materials to the reaction system, the temperature range of the reaction system is controlled to be 0±5° C.

In some embodiments of the present disclosure, in the method, wherein, the molar ratio of compound SM3-3 to reagent C is 1:12 to 17.

In some embodiments of the present disclosure, in the method, wherein, in the step of preparing compound SM3-5, when adding the materials to the reaction system, the temperature range of the reaction system is controlled to be 0±5° C.

In some embodiments of the present disclosure, in the method, wherein, in the step of preparing compound SM3-6, the molar ratio of compound SM3-5 to reducing reagent F is 1:2 to 4.

In some embodiments of the present disclosure, in the method, wherein, in the step of preparing compound SM3-7, when adding the materials to the reaction system, the temperature range of the reaction system is controlled to be 15±5° C.

In some embodiments of the present disclosure, in the method, wherein, in the step of preparing compound SM3-7, after the reagents addition is complete, the temperature range of the reaction system is controlled to be 20±5° C.

In some embodiments of the present disclosure, in the method, wherein, in the step of preparing compound SM3-7, after the completion of the reaction, the reaction system is kept under nitrogen atmosphere for filtration.

In some embodiments of the present disclosure, in the method, wherein, in the step of preparing compound SM3-7, after the reagents addition is complete, the temperature range of the reaction system is controlled to be 80±5° C.

In some embodiments of the present disclosure, in the method, wherein, in the step of preparing compound SM3-8, the pH is adjusted with acid and controlled at 2.7 to 3.5 in the post-treatment.

In some embodiments of the present disclosure, in the method, wherein, in the step of preparing compound SM3-8, the temperature range of the reaction system is controlled to be 35±5° C. when adjusting the pH in post-treatment.

In some embodiments of the present disclosure, in the method, wherein, the molar ratio of compound SM3-8 to reagent N is 1:1.5 to 2.

In some embodiments of the present disclosure, in the method, wherein, the molar ratio of compound SM3-11 to reagent Q is 1:2.5 to 4.

In some embodiments of the present disclosure, in the method, wherein, in the step of preparing compound 1-4, when adding the materials to the reaction system, the temperature range of the reaction system is controlled to be 5±5° C.

In some embodiments of the present disclosure, in the method, wherein, in the step of preparing compound 1-4, after the reagents addition is complete, the reaction time is 1.5±0.5 hours.

In some embodiments of the present disclosure, in the method, wherein, the molar ratio of compound 1-4 to base Y is 1:5.

Definition and Description

Unless otherwise specified, the following terms and phrases when used herein have the following meanings. A specific phrase or term should not be considered indefinite or unclear in the absence of a particular definition, but should be understood in the ordinary sense. When a trade name appears herein, it is intended to refer to its corresponding commodity or active ingredient thereof.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The chemical reactions of specific embodiments of the present disclosure are carried out in suitable solvents, the solvents must be suitable for the chemical changes of the present disclosure and the reagents and materials needed. In order to obtain the compounds of the present disclosure, it is sometimes necessary for those skilled in the art to modify or select the synthesis steps or reaction schemes on the basis of the existing embodiments.

An important consideration in the planning of any synthetic route in the art is the selection of appropriate protecting groups for reactive functional groups (such as amino groups in the present disclosure).

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The present disclosure is described in detail by the embodiments below, but it does not mean that there are any adverse restrictions on the present disclosure.

All solvents used in the present disclosure are commercially available and used without further purification.

The present disclosure adopts the following abbreviations: aq represents water; eq represents equivalent; DCM represents dichloromethane; PE represents petroleum ether; DMF represents N,N-dimethylformamide; DMSO represents dimethyl sulfoxide; EtOAc represents ethyl acetate; EtOH represents ethanol; MeOH represents methanol; Cbz represents benzyloxycarbonyl, which is an amine protecting group; BOC represents tert-butoxycarbonyl, which is an amine protecting group; HOAc represents acetic acid; r.t. represents room temperature; Rt represents retention time; O/N represents overnight; THF represents tetrahydrofuran; Boc$_2$O represents di-tert-butyl dicarbonate; TFA represents trifluoroacetic acid.

The compounds of the present disclosure are named according to the conventional naming principles in the art or by ChemDraw® software, and the commercially available compounds use the supplier catalog names.

Technical Effects

The process for synthesizing the compound of formula (I) and intermediates thereof provided by the present disclosure has the beneficial effects of cheap and easy-to-obtain raw materials, overcoming shortcomings such as difficulty in separation and purification and difficulty in industrialization, and avoiding the steps that are not suitable for scale-up production such as the state-regulated highly toxic methanesulfonyl chloride, hydrogenation reduction reaction of flammable and explosive sodium azide and palladium carbon, the total synthesis route is shortened, waste discharge is reduced, and more economical and practical. The present disclosure has high industrial application value and economic value in the preparation of the compound of formula (I) and the intermediate thereof.

DETAILED DESCRIPTION OF THE PREFERRED EMBODIMENT

In order to better understand the content of the present disclosure, the present disclosure is further described in conjunction with specific embodiments, but these embodiments do not limit the scope of the present disclosure.

Embodiment 1: Preparation of Compound SM1

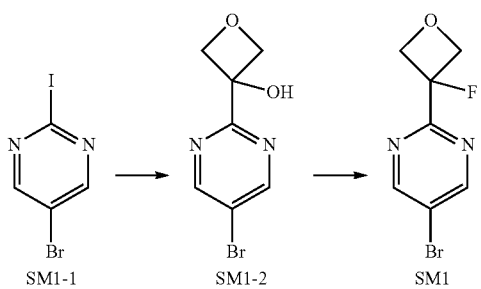 [SMILES: Brc1cnc(I)nc1 ; OC1(c2ncc(Br)cn2)COC1 ; FC1(c2ncc(Br)cn2)COC1]

Step 1:

Under the protection of nitrogen, compound SM1-1 (1.5 kg, 5.27 mol, 1 eq) was dissolved in anhydrous toluene (22.5 L), the mixture was cooled to −70 to −78° C., and n-butyllithium (2.53 L, 2.50 M n-hexane solution, 1.1 eq) was added dropwise, the reaction solution was stirred at this temperature for one hour, and a solution of oxetanone (455.32 g, 6.32 mol, 1.2 eq) in toluene (900 mL) was added dropwise, and after the completion of the dropwise addition, the reaction solution was slowly warmed to 25° C., and continued reacting for 16 hours. Saturated ammonium chloride aqueous solution (10 L) was slowly added to the reaction solution, extracted with dichloromethane (7.5 L*2), the combined organic phase was washed with saturated brine, dried over anhydrous magnesium sulfate, filtered, and the organic solvent was removed under reduced pressure, the obtained crude product was separated and purified by silica gel column chromatography (petroleum ether/tetrahydrofuran=8/1 to 5/1) to obtain 1.05 kg of compound SM1-2 (yield: 43.0%). $^1$HNMR (400 MHz, CDCl$_3$): 8.86 (s, 2H), 5.03-4.96 (m, 5H).

Step 2:

Under the protection of an ice-water bath, diethylaminosulfur trifluoride (432.54 g, 2.68 mol, 354.54 mL, 1.55 eq) was dissolved in anhydrous dichloromethane (600 mL), and a solution of compound SM1-2 (400 g, 1.73 mol, 1 eq) in anhydrous dichloromethane (2000 mL) was added dropwise. After the completion of dropwise addition, the reaction solution was slowly warmed to 25° C. and stirred for one hour. The reaction solution was cooled to 0° C., 5 L of water was added, extracted with dichloromethane (5 L*3), the combined organic phase was dried over anhydrous sodium sulfate, filtered, and the organic solvent was removed under reduced pressure, four batches of reaction solutions were combined, the crude product was separated and purified by silica gel column chromatography (petroleum ether/ethyl acetate=I/O to 10/1), and the obtained product was further recrystallized with 1.5 L petroleum ether and filtered to obtain 1.08 kg of compound SM1 (yield: 67.1%). $^1$HNMR (400 MHz, CDCl$_3$): 8.891 (s, 2H), 5.18-5.05 (m, 4H).

Embodiment 2: Preparation of Compound SM2

Step 3:

Compound SM2-1 (12.8 kg, 118.36 mol, 1.0 eq) was added to N,N-dimethylformamide (10.0 to 15.0 kg), then ethyl 2-cyanopropionate (15.0 kg, 118.36 mol, 1.0 eq) was added, the reaction solution was heated to 100 to 130° C. and stirred for 10 to 15 hours. The reaction solution was cooled to room temperature, 47.2 kg of methyl tert-butyl ether was added, and continued stirring at 25° C. for 2 to 3 hours, filtered, and the filter cake was washed with 2 to 5 kg of methyl tert-butyl ether, and the obtained solid was vacuum-dried to obtain 13.1 kg of compound SM2-2 (yield: 59.0%). $^1$HNMR (300 MHz, DMSO_d$_6$): 9.62 (s, 1H), 7.49-7.37 (m, 4H), 7.21-7.16 (m, 1H), 5.24 (s, 2H), 1.69 (s, 3H).

Step 4:

Compound SM2-2 (8.58 kg, 45.35 mol, 1.0 eq) was added to N,N-dimethylformamide (15.0 to 20.0 kg), then diisopropylethylamine (7.0 kg, 54.16 mol, 9.4 L, 1.2 eq) was added, the reaction solution was cooled to −5 to 15° C., N-phenylbis(trifluoromethanesulfon)imide (17.0 kg, 47.59 mol, 1.05 eq) was added dropwise at this temperature, and after the addition was completed, the reaction solution was warmed to 25° C. and continued stirring for 10 to 15 hours. The reaction solution was added with 60 to 80 kg of 10% aqueous sodium carbonate and 15.0 to 20.0 kg of methyl tert-butyl ether, partitioned, the organic phase was washed twice with 50 to 80 kg of 10% aqueous sodium carbonate, three times with 50 to 70 kg of saturated aqueous ammonium chloride and once with 50 to 70 kg of saturated brine, the organic solvent was removed under reduced pressure, the obtained crude product was recrystallized with 15 L of petroleum ether, filtered and the obtained solid was vacuum-dried to obtain 13.4 kg of compound SM2 (yield: 92.0%). $^1$HNMR (300 MHz, DMSO_d$_6$): 7.53-7.49 (m, 4H), 7.41-7.38 (m, 1H), 5.67 (s, 2H), 1.89 (s, 3H).

Embodiment 3: Preparation of Compound SM3

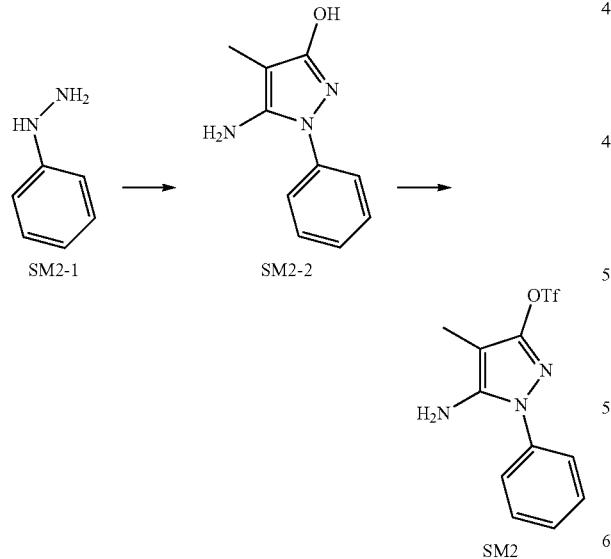

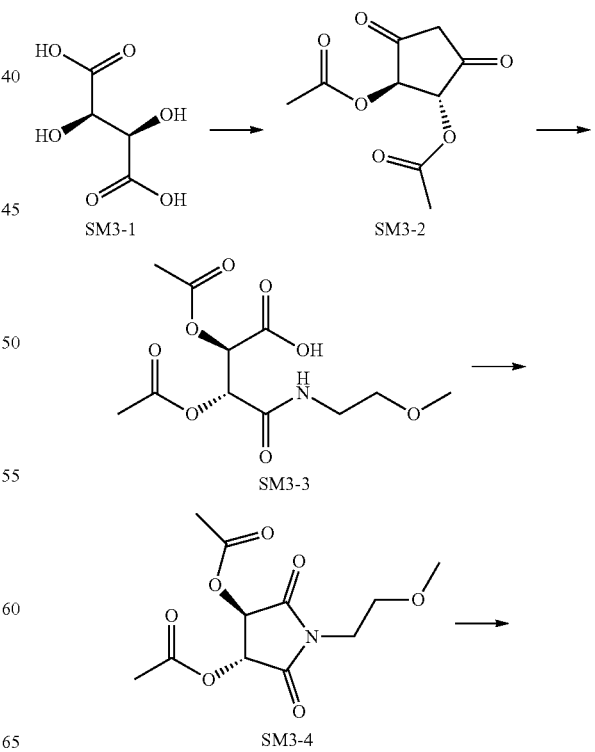

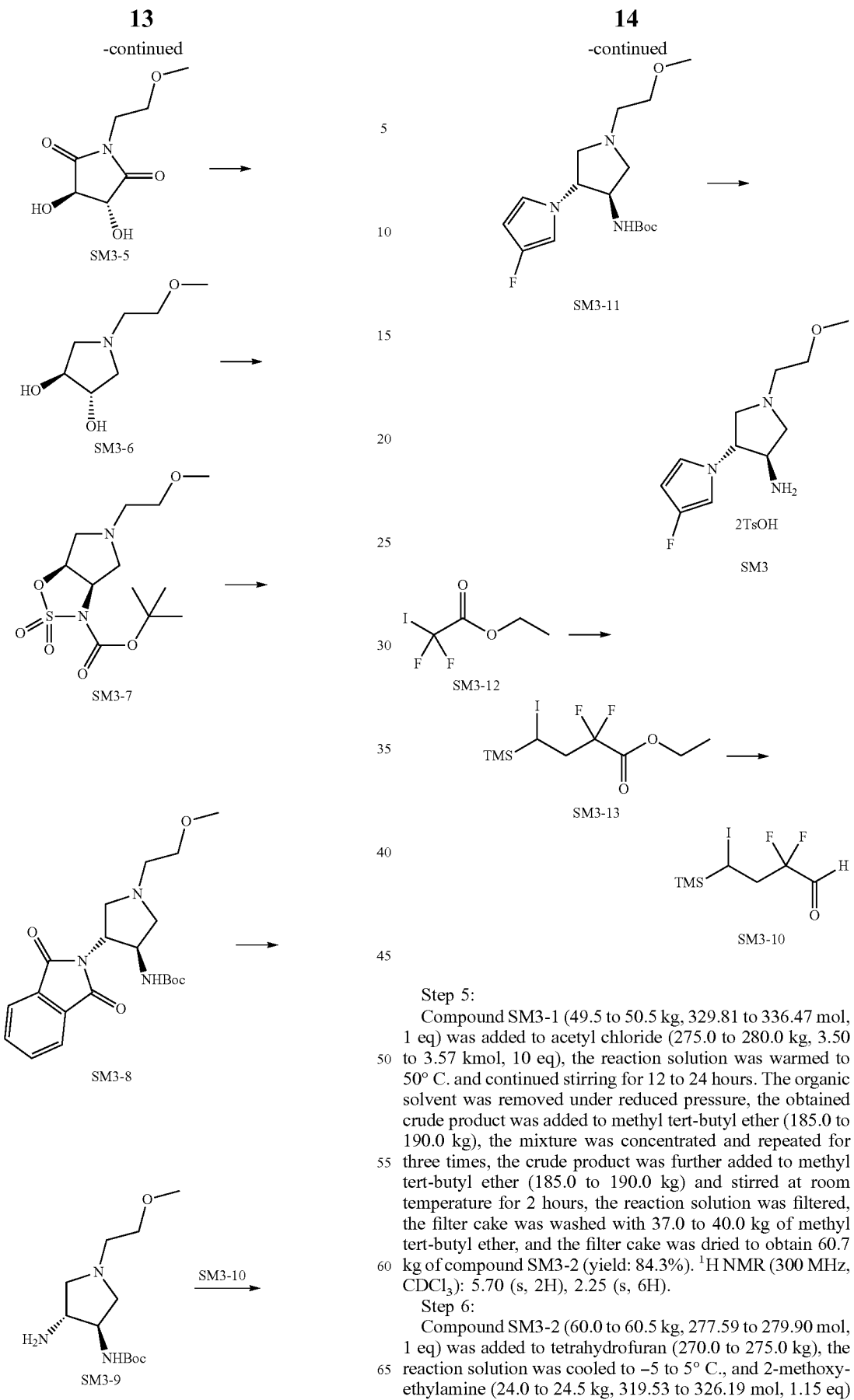

Step 5:
Compound SM3-1 (49.5 to 50.5 kg, 329.81 to 336.47 mol, 1 eq) was added to acetyl chloride (275.0 to 280.0 kg, 3.50 to 3.57 kmol, 10 eq), the reaction solution was warmed to 50° C. and continued stirring for 12 to 24 hours. The organic solvent was removed under reduced pressure, the obtained crude product was added to methyl tert-butyl ether (185.0 to 190.0 kg), the mixture was concentrated and repeated for three times, the crude product was further added to methyl tert-butyl ether (185.0 to 190.0 kg) and stirred at room temperature for 2 hours, the reaction solution was filtered, the filter cake was washed with 37.0 to 40.0 kg of methyl tert-butyl ether, and the filter cake was dried to obtain 60.7 kg of compound SM3-2 (yield: 84.3%). $^1$H NMR (300 MHz, CDCl$_3$): 5.70 (s, 2H), 2.25 (s, 6H).

Step 6:
Compound SM3-2 (60.0 to 60.5 kg, 277.59 to 279.90 mol, 1 eq) was added to tetrahydrofuran (270.0 to 275.0 kg), the reaction solution was cooled to −5 to 5° C., and 2-methoxyethylamine (24.0 to 24.5 kg, 319.53 to 326.19 mol, 1.15 eq) was added dropwise, and the temperature of the reaction solution was kept at −5 to 5° C., after the dropwise addition, the reaction solution was warmed to 65° C. and continued stirring for 2 to 24 hours. The organic solvent was removed under reduced pressure, the obtained crude product was added to methyl tert-butyl ether (224.0 to 230.0 kg), the mixture was concentrated and repeated for three times, the crude product was further added to methyl tert-butyl ether (224.0 to 230.0 kg) and stirred at room temperature for 2 hours, the reaction solution was filtered, the filter cake was washed with 45.0 to 50.0 kg of methyl tert-butyl ether to obtain 78.4 kg of compound SM3-3 (yield: 95.8%). $^1$H NMR (300 MHz, DMSO_$d_6$): 8.15 (brs, 1H), 5.45 (d, J=2.4 Hz, 1H), 5.37 (d, J=2.4 Hz, 1H), 5.26 (brs, 1H), 3.50 (t, J=5.4 Hz, 2H), 3.20 (s, 3H), 2.96 (t, J=5.4 Hz, 2H), 2.09 (s, 3H), 2.02 (s, 3H).

Step 7:

Compound SM3-3 (78.3 kg, 268.84 mol, 1 eq) was added to acetyl chloride (360.0 to 365.0 kg, 4.59 to 4.65 kmol, 17 eq), the reaction solution was warmed to 50° C. and continued stirring for 12 to 24 hours. The organic solvent was removed under reduced pressure, and the obtained crude product was added to methyl tert-butyl ether (290.0 to 300.0 kg), the mixture was concentrated and repeated three times, the crude product was added to methyl tert-butyl ether (232.0 to 240.0 kg) and ethyl acetate (140.0 to 145.0 kg), washed with 315.0 to 320.0 kg of 8% sodium bicarbonate aqueous solution, the aqueous phase was extracted for three times with ethyl acetate (282.0 to 290.0 kg), and the combined organic phase was washed with saturated brine (315.0 to 320.0 kg), the organic solvent was removed under reduced pressure, ethanol (186.0 to 190.0 kg) was added to the obtained crude product, the mixture was concentrated and repeated twice, 390.0 to 395.0 kg ethanol was added to obtain an ethanol solution of compound SM3-4, which was used directly in the next reaction step without further purification. $^1$H NMR (300 MHz, DMSO_$d_6$): 5.78 (s, 2H), 3.60 (m, 2H), 3.45 (d, 2H), 3.23 (s, 3H), 2.15 (s, 6H).

Step 8:

The solution of the compound SM3-4 (73.5 kg, 268.99 mol, 1 eq) in ethanol was cooled to −5 to 5° C., acetyl chloride (150.0 to 155.0 kg, 1.91 to 1.97 kmol, 7 eq) was added dropwise, and the reaction solution was warmed to 20 to 30° C. and continued stirring for 5 to 24 hours. Activated carbon (5.0 to 5.5 kg) was added and continued stirring for 2 to 5 hours. The mixture was filtered, the filter cake was washed with ethanol (115.0 to 120.0 kg), the organic solvent was removed under reduced pressure, the obtained crude product was added to methyl tert-butyl ether (240.0 to 250.0 kg), the mixture was concentrated and repeated for three times, the crude product was further added to methyl tert-butyl ether (240.0 to 190.0 kg) and stirred at room temperature for 2 to 5 hours, the reaction solution was filtered, the filter cake was washed with 100.0 to 105.0 kg of methyl tert-butyl ether, and the filter cake was dried to obtain 33.7 kg of compound SM3-5 (content: 88%, yield: 66.0%). $^1$HNMR (300 MHz, DMSO_$d_6$): 5.58 (brs, 2H), 4.30 (s, 2H), 3.53 (m, 2H), 3.44 (m, 2H), 3.21 (s, 3H).

Step 9:

Under the protection of nitrogen, flake lithium aluminum hydride (200 g, 5.29 mol, 4 eq) was dissolved in anhydrous tetrahydrofuran (5000 mL), and a solution of compound SM3-5 (284 g, 88% content, 1.32 mol, 1 eq) in tetrahydrofuran (2000 mL) was added, the reaction solution was warmed to 60 to 70° C. and stirred for 16 hours. The reaction solution was cooled to 20 to 30° C., sodium sulfate decahydrate (284 g, 1.32 mol, 1 eq), water (284 mL) and 20% aqueous sodium hydroxide solution (284 mL) were sequentially added, and the reaction solution was warmed to 60° C. and continued stirring for one hour. The reaction solution was filtrated, the filter cake was washed twice with 4000 mL of tetrahydrofuran, the obtained filter cake was added to 4000 mL of tetrahydrofuran and 500 mL of 20% aqueous sodium hydroxide solution, 500 g of anhydrous sodium sulfate was added, the mixture was filtered, the organic phases were combined, and 41 batches the organic phases were combined, the organic phase was removed under reduced pressure to obtain 4.34 kg of compound SM3-6 (content: 83%, yield: 41.2%). $^1$HNMR (400 MHz, DMSO_$d_6$): 4.87 (s, 2H), 3.95-3.93 (m, 2H), 3.27 (s, 3H), 2.85-2.80 (m, 2H), 2.61-2.49 (m, 2H), 2.40-2.36 (m, 2H).

Step 10:

Under the protection of nitrogen, sulfonic acid isocyanate (614.6 g, 4.34 mol, 3.5 eq) was dissolved in anhydrous 1,4-dioxane (800 mL), the reaction solution was cooled to 10 to 20° C., and a solution of tert-butanol (321.9 g, 4.34 mol, 3.5 eq) in 1,4-dioxane (600 mL) was slowly added, the internal temperature was kept at 10 to 20° C., and the mixture was continued stirring for 0.5 hours after the dropwise addition, and the obtained solution was used for later use. Under the condition of ice-water bath, compound SM3-6 (241 g, 83% content, 1.25 mol, 1 eq) was dissolved in anhydrous 1,4-dioxane (4000 mL), and triethylamine (753 g, 7.44 mol, 6 eq) was added, and then the standby solution was slowly added dropwise, and the temperature of the reaction solution was kept below 20° C., after the completion of the dropwise addition, the reaction solution was stirred at 25° C. for 4 hours. The reaction solution was filtrated under nitrogen protection, the filter cake was washed once with anhydrous dioxane, triethylamine (213 g, 2.1 mol, 1.7 eq) was added to the filtrate, and the reaction solution was warmed to 82° C. and continued stirring for 4 hours. The temperature of the reaction system was cooled down, the organic solvent was removed under reduced pressure, 2000 mL of water and 2000 mL of ethyl acetate were added, partitioned, the aqueous phase was continued to extract once with 2000 mL of ethyl acetate, the organic solvent was removed from the combined organic phases under reduced pressure, and 12 batches crud product were combined, which was separated and purified by silica gel column chromatography (petroleum ether to petroleum ether: ethyl acetate=4:1) to obtain 2.68 kg of compound SM3-7 (content: 71%, yield: 39.6%). $^1$HNMR (400 MHz, DMSO_$d_6$): 5.35-5.32 (m, 1H), 4.73-4.70 (m, 1H), 3.52-3.49 (m, 2H), 3.12 (s, 3H), 3.12-3.08 (m, 1H), 3.02-2.98 (m, 1H), 2.86-2.82 (m, 2H), 2.73-2.70 (m, 2H), 1.53 (m, 9H).

Step 11:

Under the protection of nitrogen, compound SM3-7 (1.41 kg, 71% content, 3.0 mol, 1 eq) was dissolved in N,N-dimethylformamide (5000 mL), and phthaloyl potassium salt (747 g, 4.0 mol, 1.3 eq) was added, the reaction solution was warmed to 70° C. and stirred for 8 hours. The temperature of the reaction was cooled down, and the reaction solution was filtered through diatomite, and the organic solvent was removed under reduced pressure, the obtained residue was dissolved in 2000 mL of tetrahydrofuran, the pH was adjusted to 2.7 to 3.5 with 0.5 M aqueous hydrochloric acid solution, and the reaction solution was warmed to 40° C. and continued stirring for one hour. The mixture was cooled down, extracted with methyl tert-butyl ether (4000 mL), the pH of aqueous phase was adjusted to 8 to 9 with 20% aqueous sodium carbonate solution, the other two batches were combined and filtered, the filter cake was washed with water, and dried to obtain 6.0 kg of compound SM3-8 (content: 60%, yield: 81.0%). $^1$H NMR (400 MHz, DMSO_d₆): 7.83-7.71 (m, 4H), 5.25-5.22 (m, 1H), 4.64-4.58 (m, 2H), 3.52-3.46 (m, 2H), 3.33 (s, 3H), 3.24-3.20 (m, 1H), 3.08-3.04 (m, 1H), 2.95-2.88 (m, 1H), 2.78-2.70 (m, 3H), 1.38 (s, 9H).

Step 12:

Under the protection of nitrogen, compound SM5-8 (600 g, 60% content, 0.92 mol, 1 eq) was dissolved in N,N-dimethylformamide (7.2 L), and hydrazine hydrate (108.7 g, 1.85 mol, 2 eq) was added, the reaction solution was warmed to 70° C. and continued stirring for one hour. The mixture was cooled, filtered, the organic solvent was removed under reduced pressure, 6 batches crude product were combined, methyl tert-butyl ether (6000 mL) was added, the mixture was filtered, the organic solvent was removed under reduced pressure to obtain 1.35 kg of compound SM3-9 (yield: 92.0%). ¹H NMR (400 MHz, CDCl₃): 4.79 (s, 1H), 3.54-3.52 (m, 1H), 3.32-3.29 (m, 2H), 3.20 (s, 3H), 3.11 (s, 1H), 2.70-2.66 (m, 1H), 2.51-2.40 (m, 3H), 1.99-1.95 (m, 1H), 1.42 (s, 9H).

Step 13:

Compound SM3-12 (750 g, 3.00 mol, 1 eq) and vinyltrimethylsilane (601.45 g, 6.00 mol, 870.40 mL, 2 eq) were dissolved in acetonitrile (1.8 L), and activated copper powder was added (9.53 g, 150.01 mmol, 0.05 eq), the reaction solution was warmed to 65° C. and continued stirring for 18 hours. The organic solvent was removed under reduced pressure, and 4 batches crude product were combined, which was separated and purified by silica gel column chromatography (eluent: 0 to 3% ethyl acetate/petroleum ether) to obtain 3.80 kg of compound SM3-13 (yield: 90.5%). ¹H NMR (400 MHz, CDCl₃): 4.25-4.12 (m, 2H), 2.93-2.90 (m, 1H), 2.47-2.39 (m, 2H), 1.24-1.13 (m, 3H), 0.02 (s, 9H).

Step 14:

Compound SM3-13 (1.27 kg, 3.63 mol, 1 eq) was dissolved in anhydrous tetrahydrofuran (15 L) at −20° C., and diisobutylaluminum hydride (1 M toluene solution, 5.44 L, 1.5 eq) was slowly added dropwise, the reaction solution was slowly warmed to 10° C. and continued stirring for 1 hour. The temperature of the reaction solution was cooled down, 5 L of 2N aqueous hydrochloric acid solution was slowly added dropwise, and the temperature of the reaction solution was kept below 20° C., the mixture was extracted with ethyl acetate (8 L*2), the extracted organic phases were combined, washed with 10 L of saturated brine, dried over anhydrous sodium sulfate, filtered, and the organic solvent was removed under reduced pressure to obtain 977.5 g of compound SM3-10 (yield: 88.0%). The compound was used in the next reaction without further purification.

Step 15:

Compound SM3-9 (690 g, 2.66 mol, 1 eq) was dissolved in acetonitrile (6.5 mL), and SM3-10 (977.48 g, 3.19 mol, 1.2 eq) was added, the reaction solution was warmed to 65° C. and continued stirring for 14 hours. The organic solvent was removed under reduced pressure, and the other batch crude product was combined, which was separated and purified by silica gel column chromatography (eluent: 0 to 60% ethyl acetate/petroleum ether to 5% methanol/ethyl acetate) to obtain 1.70 kg of compound SM3-11 (yield: 98%). ¹H NMR (400 MHz, CDCl₃): 6.74 (s, 1H), 6.50 (s, 1H), 5.77 (s, 1H), 5.64 (s, 1H), 4.85 (s, 1H), 4.48 (s, 1H), 3.81-3.58 (m, 6H), 3.41-3.38 (m, 2H), 3.23 (s, 3H), 1.19 (s, 9H).

Step 16:

Compound SM3-11 (2.86 kg, 8.74 mol, 1 eq) was dissolved in anhydrous tetrahydrofuran (22 L), and p-toluenesulfonic acid (3.76 kg, 21.84 mol, 2.5 eq) was added, the reaction solution was warmed to 80° C. and continued stirring for 2 hours. The mixture was cooled down, filtered, and the filter cake was washed with methyl tert-butyl ether (300 mL*2) and dried to obtain 3.30 kg of compound SM3 (yield: 66.1%). ¹H NMR (400 MHz, MeOD): 7.76-7.74 (m, 4H), 7.30-7.28 (m, 4H), 6.86-6.84 (m, 1H), 6.78-6.75 (m, 1H), 6.01-5.99 (m, 1H), 5.11-5.09 (m, 1H), 4.44-4.41 (m, 1H), 4.15-4.11 (m, 2H), 3.85-3.70 (m, 4H), 3.62-3.59 (m, 2H), 3.38 (s, 3H), 2.40 (s, 6H).

Embodiment 4: Preparation of Compound 1

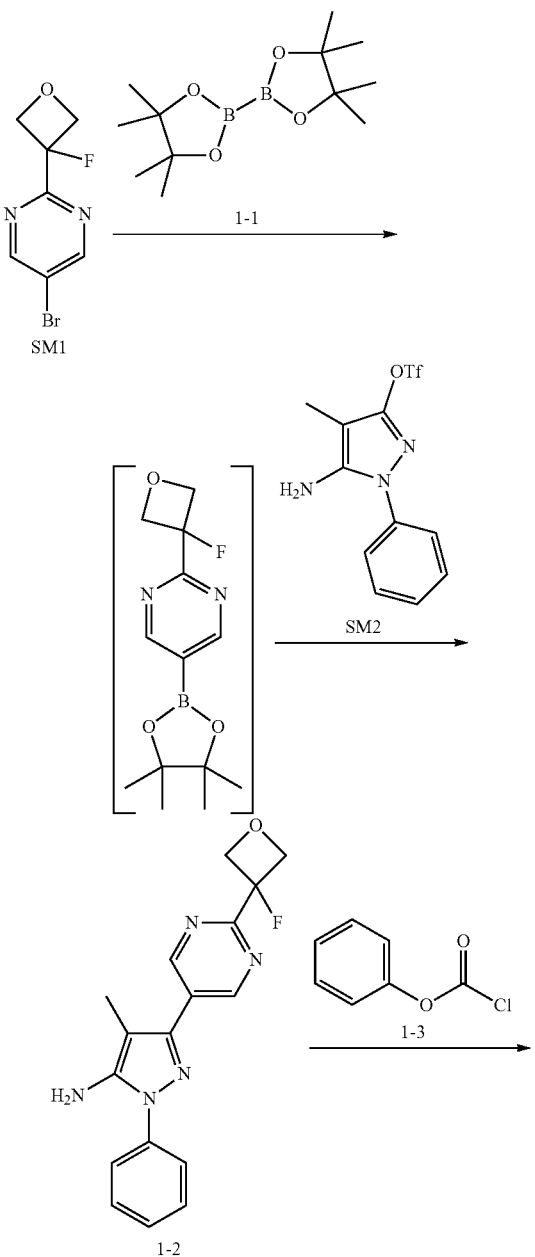

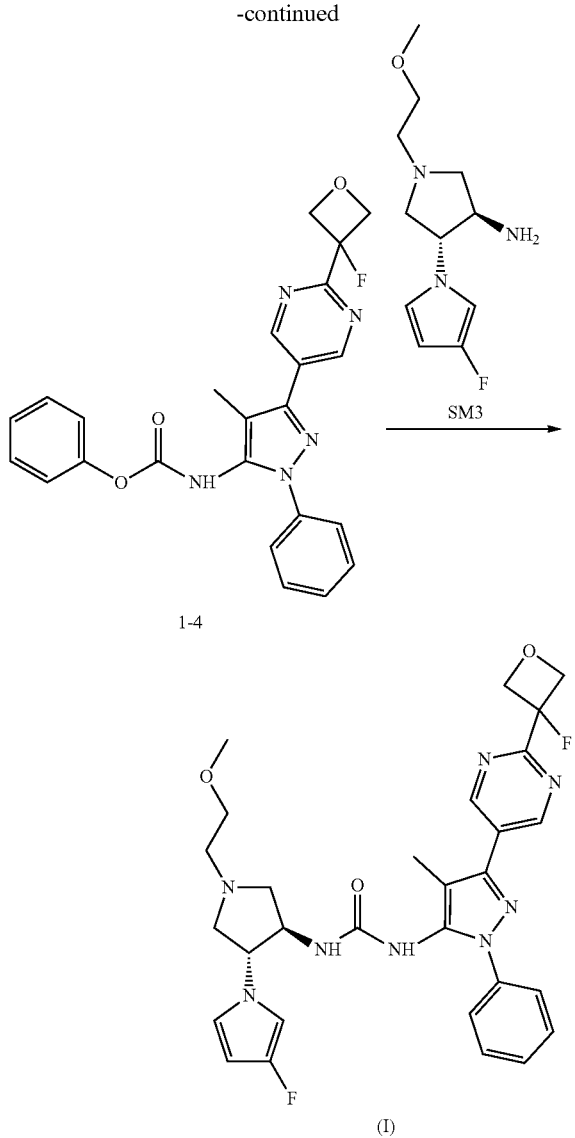

Step 17:

Under the protection of nitrogen, compound SM1 (1.0 kg, 4.30 mol, 1 eq) was dissolved in anhydrous dioxane (30.0 L), bis(pinacolato)diboron (1.2 kg, 4.74 mol, 1.1 eq), potassium acetate (840 g, 8.62 mol, 2 eq), tricyclohexylphosphane (120 g, 430.0 mmol, 0.1 eq) and palladium acetate (100 g, 430 mmol, 0.1 eq) were sequentially added thereto, the reaction solution was warmed to 90° C. and continued stirring for 3 hours, water (5 L), SM2 (1.1 kg, 3.45 mol, 0.8 eq), sodium carbonate (1.0 kg, 8.62 mol, 2 eq) and (diphenylphosphino)ferrocene dichloropalladium(II) (300 g, 430.0 mmol, 0.1 eq) were sequentially added to the reaction solution and the reaction solution was stirred at this temperature for 15 to 18 hours. The reaction solution was cooled to room temperature, filtered through diatomite, the filter cake was washed with ethyl acetate (5 L), the combined filtrate was added with saturated brine (10 L) for separation, and the aqueous phase was extracted with ethyl acetate (10 L*2), the combined organic phase was concentrated under reduced pressure to 30 L, activated carbon (2.0 kg), anhydrous magnesium sulfate (4.0 kg) and metal scavenger (3-mercaptopropyl functional silica gel, 2.0 kg) were added, and the temperature was warmed to 55° C. and continued stirring for 18 hours, the reaction solution was filtered through diatomite, the filter cake was washed with ethyl acetate (10 L*2), the organic solvent was removed under reduced pressure, and the crude product was added to methyl tert-butyl ether (5 L), n-heptane (1 L) was added and continued stirring at room temperature for 15 to 18 hours, filtered, the filter cake was washed with methyl tert-butyl ether (500 mL*2), dried, and the crude product was added to acetonitrile (3.5 L), water (15 to 17 L) was added, the mixture was warmed to 80° C. and stirred for 15 hours, filtered, and the filter cake was washed with water (500 mL*2) and dried to obtain 0.47 kg of compound 1-2 (yield: 40.0%). $^1$H NMR (400 MHz, CDCl$_3$): 9.20 (s, 2H), 7.68-7.62 (m, 2H), 7.57-7.53 (m, 2H), 7.48-7.40 (m, 1H), 5.29-5.13 (m, 4H), 3.76 (brs, 2H), 2.19 (s, 3H).

Step 18:

Under the protection of nitrogen, compound 1-2 (0.73 kg, 2.24 mol, 1 eq) was dissolved in anhydrous dichloromethane (15 L), pyridine (0.54 kg, 6.74 mol, 3 eq) was added, the mixture was cooled to 0° C., and a solution of compound 1-3 (0.46 kg, 2.92 mol, 1.3 eq) in dichloromethane (1.2 L) was added dropwise, and the internal temperature of the reaction solution was kept below 10° C., after the completion of the dropwise addition, the reaction solution was continued stirring at this temperature for 0.5 to 2 hours. 0.5N aqueous hydrochloric acid (8 L) was added to the reaction solution, the mixture was partitioned, the aqueous phase was extracted with dichloromethane (8 L), the combined organic phase was washed with saturated brine (10 L), and dried over anhydrous sodium sulfate, filtrated and the organic solvent was removed under reduced pressure to obtain 0.90 kg of compound 1-4 (yield: 90.0%), which was used in the next reaction without further purification. $^1$H NMR (400 MHz, CDCl$_3$): 9.26 (s, 2H), 7.64-7.40 (m, 6H), 7.53-7.48 (m, 2H), 7.32-7.29 (m, 1H), 7.15-7.12 (m, 1H), 5.31-5.12 (m, 4H), 2.35 (s, 3H).

Step 19:

Compound 1-4 (1.0 kg, 2.24 mol, 1 eq) was dissolved in anhydrous tetrahydrofuran (10 L), compound SM3 (1.28 kg, 2.24 mol, 1 eq) was added, and a solution of sodium carbonate (1.19 kg, 11.23 mol, 5 eq) in water (5.0 L) was added dropwise, the reaction solution was stirred at room temperature for 20 hours. The reaction solution was added to water (6.0 L) and ethyl acetate (6.0 L) to partition, the aqueous phase was extracted with ethyl acetate (6.0 L*2), the combined organic phase was washed with saturated brine (15.0 L), dried over anhydrous sodium sulfate, filtered, the organic solvent was removed under reduced pressure, the obtained crude product was added to methanol (6.5 L), water (13 L) was added, the mixture was warmed to 40° C. and stirred for 10 to 48 hours, filtered and the filter cake was washed with water (2 L*2) and dried to obtain 0.93 kg of compound 1 (yield: 71.6%). $^1$H NMR (400 MHz, MeOD): 9.27 (s, 2H), 7.61-7.50 (m, 4H), 7.49-7.42 (m, 1H), 6.64-6.59 (m, 1H), 6.56-6.50 (m, 1H), 5.84 (m, 1H), 5.32-5.21 (m, 2H), 5.12-5.02 (m, 2H), 4.34-4.18 (m, 2H), 3.55-3.53 (t, J=5.2 Hz, 2H), 3.37 (s, 3H), 3.14-3.06 (m, 2H), 2.89-2.64 (m, 3H), 2.55-2.50 (m, 1H), 2.23 (s, 3H).

Experimental Example 1: TrkA Enzyme Activity Test

Experimental Materials

TrkA Invitrogen-PV4114

TK detection kit Cisbio-62TK0PEJ

Detection plate PerkinElmer-6007299

Envision PerkinElmer-2104

Kinase Reaction Buffer 20 mM Hepes (pH 7.5), 10 mM $MgCl_2$ (magnesium chloride), 1 mM EGTA, 0.01% Brij35, 0.1 mM Orthovanadate (sodium vanadate), 0.02 g/mL BSA (bovine serum protein), 2 mM DTT (dithiothreitol), 1% DMSO Experimental Method This experiment was performed using Cisbio's homogeneous time-resolved fluorescence conjugate energy transfer (HTRF® method) for activity detection. In the detection plate, enzyme, biotin-labeled peptide substrate, ATP and detection compound were mixed and incubated for reaction. After the reaction, EDTA was added to terminate the reaction, and at the same time, Eu-labeled antibody and streptavidin-labeled XL665 were added for reaction and detection. The data were represented by fluorescence signal readings at 665 nm and 620 nm respectively, with a high ratio of 665 nm/620 nm indicating high activity and a low ratio of 665 nm/620 nm indicating inhibition of activity.

Experimental Steps

Compound dilution: the compound to be tested was 4-fold diluted, with a total of 10 concentrations, and the final system concentration was from 10 μM to 0.038 nM;

In a 10 μL reaction system with a buffer of 20 mM Hepes (pH 7.5), 10 mM $MgCl_2$, 1 mM EGTA, 0.01% Brij35, 0.1 mM sodium vanadate, 0.02 g/mL BSA, 2 mM DTT, 1% DMSO medium, containing 15 nM TrkA kinase, 0.3 μM biotin-TK peptide (biotin-labeled tyrosine kinase substrate polypeptide), 100 μM ATP were incubated at 23° C. for 120 minutes. The reaction was spotted on P81 ion exchange paper (Whatman #3698-915), the filter was washed thoroughly with 0.75% phosphoric acid, and the radiophosphorylated substrate remaining on the filter was measured. Kinase activity data were expressed as a percentage of kinase activity in the test sample compared to the vehicle (DMSO) reaction.

$IC_{50}$ and curve fitting can be obtained by Graphpad software Prism4.

Experimental Result

The result is shown in Table 1:

TABLE 1

| $IC_{50}$ value of compound of formula (1) for inhibition of TrkA enzyme | |
| --- | --- |
| Compound number | Trk $AIC_{50}$ (nM) |
| Compounds of formula (1) | 6.64 |

The result shows that the compound of formula (I) has a significant inhibitory effect on TrkA enzyme.

Experimental Example 2: Cytochrome P450 Isoenzyme Inhibitory Activity Test

Experimental Purpose

The inhibitory activities of test compound against different isoforms of human cytochrome P450 isoenzymes were determined.

Experimental Operation

The test compound, standard inhibitor (100×final concentration) and mixed substrate working solution were prepared; the microsome frozen in −80° C. refrigerator was taken out and thawed. 2 μL of the compound to be tested and standard inhibitor solution were added to the corresponding wells, and at the same time, 2 μL of the corresponding solvent was added to the non-inhibitor control wells (NIC) and the blank control wells; secondly, 20 μL of mixed substrate solution was added to the corresponding wells except the blank wells (20 μL of Pb was added to the blank wells); human liver microsome solution was prepared (the solution was put back in the refrigerator immediately after using and marking the date), and then 158 μL of human liver microsome solution was added to all wells; the sample plate was put in a 37° C. water bath for pre-incubation, and then a coenzyme factor (NADPH) solution was prepared; after 10 minutes, 20 μL of NADPH solution was added to all wells, the sample plate was shaken well, and incubated in a 37° C. water bath for 10 minutes; at the corresponding time point, 400 μL of cold acetonitrile solution (internal standard is 200 ng/mL tolbutamide and labetalol) was added to terminate the reaction; after the plates were evenly mixed, the mixture was centrifuged at 4000 rpm for 20 minutes to precipitate protein; 200 μL of supernatant was added into 100 μL of water, shaken well and detected by LC/MS/MS.

Experimental Results

The results are shown in Table 3.

TABLE 3

| $IC_{50}$ values of compound of formula (1) for inhibition of P450 isoenzyme | | | | | |
| --- | --- | --- | --- | --- | --- |
| Compound number | Cytochrome P450 isoenzyme IC50 (nM) | | | | |
| | CYP1A2 | CYP2C9 | CYP2C19 | CYP2D6 | CYP3A4 |
| Compounds of formula (1) | >50 | 43.6 | >50 | 31.7 | >50 |

The results show that the compound of formula (I) has a lower risk of drug-drug interaction.

Experimental Example 3: In Vivo Pharmacokinetics Study after Single Administration in Rats Experimental Purpose Male SD rats were used as the test animals, and the plasma concentrations of the compound were determined after a single administration and the pharmacokinetic behavior was evaluated.

Experimental Materials

Sprague Dawley rats (male, 200 to 300 g, 7 to 9 weeks old, Shanghai Charles River Laboratory Animal Co., LTD.)

Experimental Operation

Standard protocols were used to test the pharmacokinetic characteristics of the tested compounds in rodents after intravenous injection and oral administration, in the experiment, the tested compounds were prepared into a clear solution or a homogeneous suspension, and the rats were given a single intravenous injection and oral administration. In the intravenous injection group, the solvent was a certain proportion of ethanol and normal saline solution or a certain proportion of HP-β cyclodextrin solution of dimethyl sulfoxide (the pH was adjusted 3 to 4), the mixture was vortex-stirred to prepare 1 mg/mL clear solution and filtered by a microporous membrane for later use; oral solvent was a certain proportion of sodium carboxymethyl cellulose solution or a certain proportion of HP-β cyclodextrin solution of dimethyl sulfoxide (the pH was adjusted to above 4), after the compound to be tested was mixed with the solvent, the mixture was vortex-stirred to obtain a uniform suspension of 30 mg/mL for later use. After intravenous administration of 2 mg/kg or oral administration of 300 mg/kg to rats, a certain amount of whole blood samples were collected, the samples were centrifuged at 3000 g for 15 minutes, and the supernatant was separated to obtain plasma samples, the samples were precipitated protein by adding 3 times the volume of acetonitrile solution containing internal standard, centrifuged and the supernatant was taken, 2 times the volume of water was added, then centrifuged, the supernatant was taken for injection, the blood drug concentration was quantitatively analyzed by LC-MS/MS analysis method, and Phoenix WinNonlin software (Pharsight, USA) was used to calculate the pharmacokinetic parameters, such as peak concentration, peak time, clearance rate, half-life, area under the drug concentration-time curve, bioavailability, etc.

Experimental Results

TABLE 5

Pharmacokinetic properties of compounds of formula (1) in male rats (n = 3)

| Compound number | | Compounds of formula (1) |
|---|---|---|
| 2 mpk intravenous injection | $C_0$ (ng/mL) | 3620 |
| | $T_{1/2}$ (hr) | 0.61 |
| | $Vd_{ss}$ (L/kg) | 0.70 |
| | Cl (mL/min/kg) | 17.1 |
| | $AUC_{0\text{-}inf}$ (ng · hr/mL) | 1970 |
| 300 mpk oral | $C_{max}$ (ng/mL) | 47600 |
| | $T_{max}$ (hr) | 1.50 |
| | $T_{1/2}$ (hr) | 1.70 |
| | $AUC_{0\text{-}inf}$ (ng · hr/mL) | 210000 |
| | Bioavailability | 71.1% |

$C_0$ is the initial concentration, $T_{1/2}$ is the elimination half-life, $V_{dss}$ is the steady-state apparent volume of distribution, Cl is the total clearance, and $AUC_{0\text{-}inf}$ is area under the plasma drug concentration-time curve from 0 time to extrapolation to infinity area, $C_{max}$ is the peak concentration, and $T_{max}$ is the peak time.

The results show that the compound of formula (I) have good pharmacokinetic properties and oral bioavailability in rats.

Experimental Example 4: In Vivo Pharmacokinetics Study after Single Administration in Beagle Dogs Experimental Purpose Male Beagle dogs were used as the test animals, and the plasma concentrations of the compounds were determined after a single administration and the pharmacokinetic behavior was evaluated.

Experimental Materials

Beagle (male, 6 to 12 kg, more than 6 months old, Beijing Mars Biotechnology Co., Ltd.)

Experimental Operation

The purpose of the experiment was to test the pharmacokinetic characteristics of the tested compounds in non-rodents after intravenous injection and oral administration, in the experiment, the tested compounds were prepared into a clear solution or a homogeneous suspension, and the beagle dogs were given a single intravenous injection or oral administration. In the intravenous injection group, the solvent was a certain proportion of HP-β-cyclodextrin solution of dimethyl sulfoxide or a certain proportion of ethanol, and a normal saline solution of polyethylene glycol 400, vortexed and ultrasonicated to prepare a 2 mg/kg clear solution and filtered by microporous membrane for later use; oral solvent was a certain proportion of HP-β cyclodextrin solution of dimethyl sulfoxide or a certain proportion of sodium carboxymethyl cellulose solution, after the compound to be tested was mixed with the solvent, the solvent was vortexed and ultrasonicated to prepare a 3 mg/mL uniform suspension for later use. After intravenous administration of 2 mg/kg or oral administration of 15 mg/kg to Beagle dogs, a certain amount of whole blood samples were collected, the samples were centrifuged at 3000 g for 10 minutes, and the supernatant was separated to obtain plasma samples, the samples were precipitated protein by adding 10 times the volume of acetonitrile solution containing internal standard, centrifuged and the supernatant was taken for injection, the blood drug concentration was quantitatively analyzed by LC-MS/MS analysis method, and Phoenix WinNonlin software (Pharsight, USA) was used to calculate the pharmacokinetic parameters, such as peak concentration, peak time, clearance rate, half-life, area under the drug concentration-time curve, bioavailability, etc.

Experimental Results

TABLE 7

Pharmacokinetic properties of compounds of formula (I) in male Beagle dogs (n = 3)

| Compound number | | Compounds of formula (I) |
|---|---|---|
| 2 mpk intravenous injection | $C_0$ (ng/mL) | 3940 |
| | $T_{1/2}$ (hr) | 0.72 |
| | $Vd_{ss}$ (L/kg) | 0.71 |
| | Cl (mL/min/kg) | 18.4 |
| | $AUC_{0\text{-}inf}$ (ng · hr/mL) | 1840 |
| 15 mpk oral | $C_{max}$ (ng/mL) | 4560 |
| | $T_{max}$ (hr) | 1.00 |
| | $T_{1/2}$ (hr) | 1.20 |
| | $AUC_{0\text{-}inf}$ (ng · hr/mL) | 12600 |
| | Bioavailability | 91.3% |

$C_0$ is the initial concentration, $T_{1/2}$ is the elimination half-life, $V_{dss}$ is the steady-state apparent volume of distribution, Cl is the total clearance, and $AUC_{0\text{-}inf}$ is area under the plasma drug concentration-time curve from 0 time to extrapolation to infinity area, $C_{max}$ is the peak concentration, and $T_{max}$ is the peak time.

The results show that the compound of formula (I) have good pharmacokinetic properties and oral bioavailability in beagle dogs.

What is claimed is:

1. A method for preparing of a compound represented by formula (I),

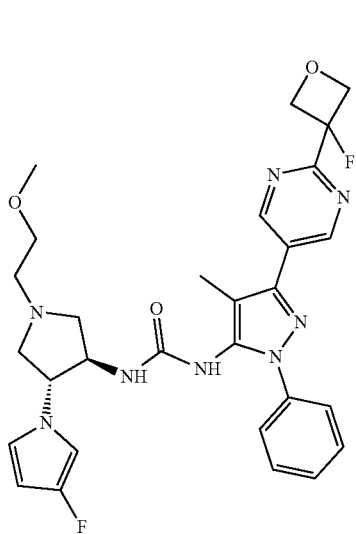

(I)

comprising the following steps:

step 1-1: reacting a compound represented by formula SM3-9 with a compound represented by formula SM3-10 to obtain a compound represented by formula SM3-11,

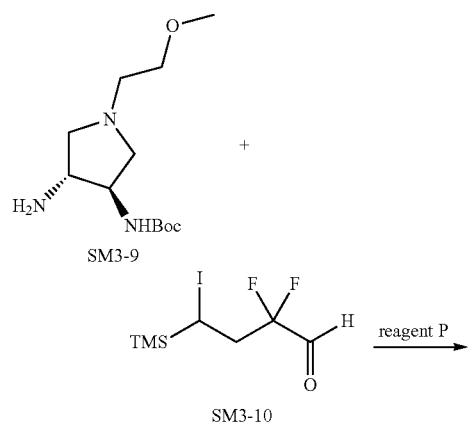

step 1-2: reacting the compound represented by formula SM3-11 with a reagent Q to obtain a compound represented by formula SM3,

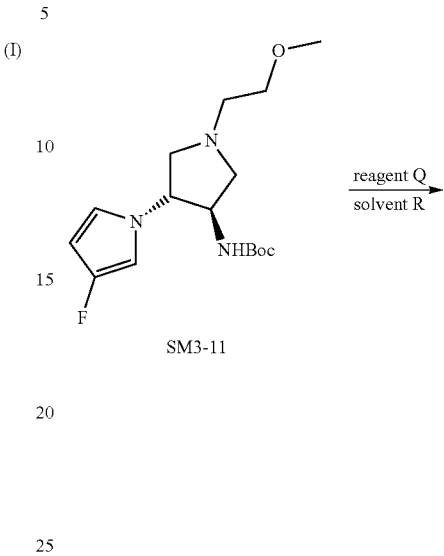

step 2:1: reacting a compound represented by formula SM1 with a compound represented by formula 1-1 to obtain an intermediate compound, and which is reacted with a compound represented by formula SM2 to obtain a compound represented by formula 1-2,

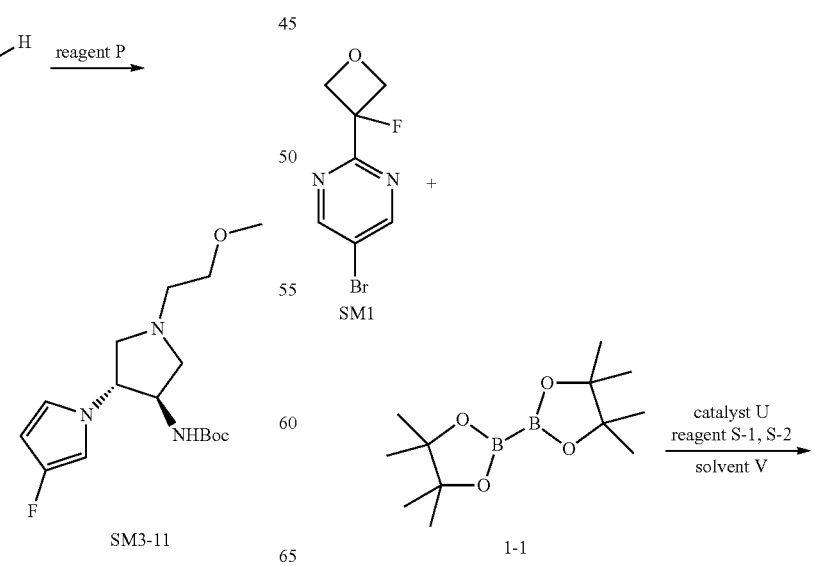

27
-continued
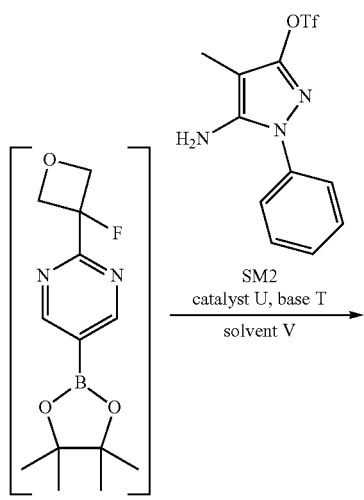
28
-continued
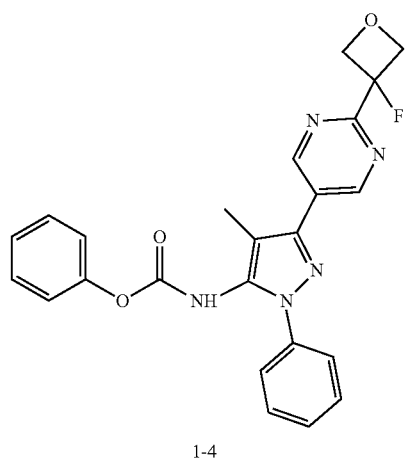
1-4
step 3: reacting the compound represented by formula 1-4 with the compound represented by formula SM3 to obtain the compound represented by formula (I),
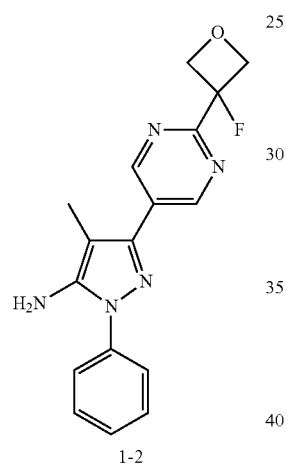
1-2
step 2-2: reacting the compound represented by formula 1-2 with a compound represented by formula 1-3 to obtain a compound represented by formula 1-4,
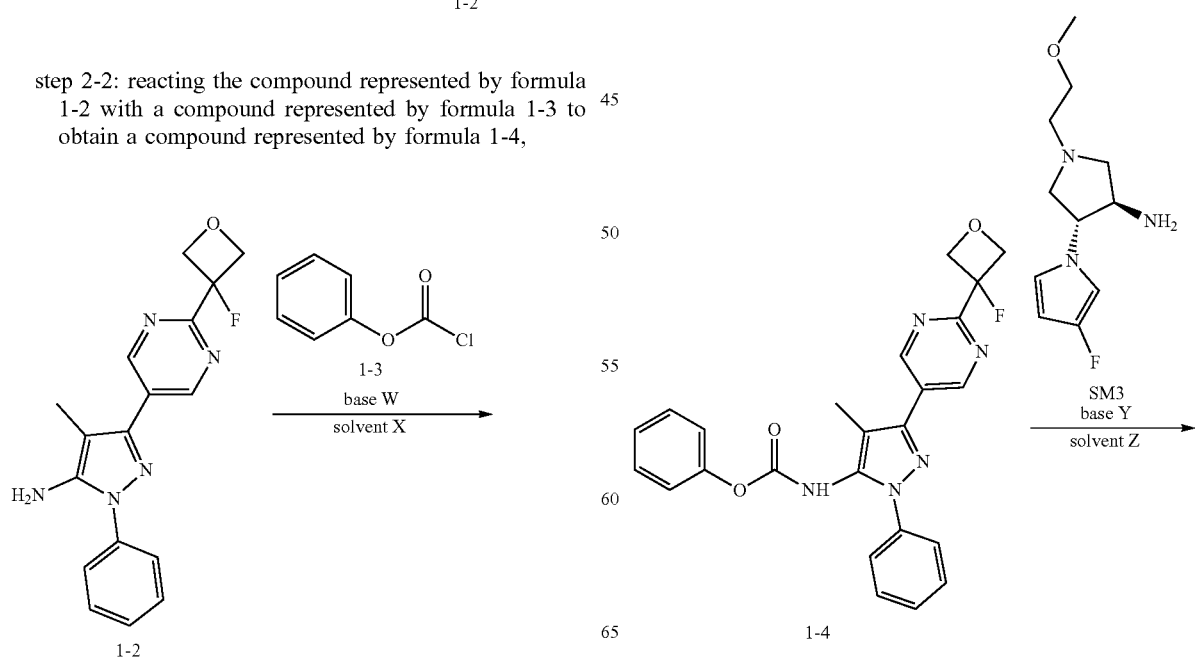

-continued

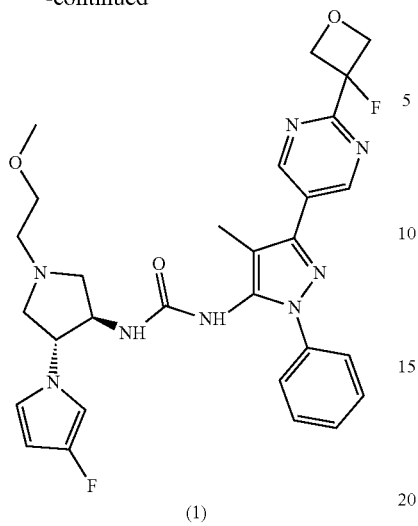

(1)

wherein, reagent P is acetonitrile;

reagent S-1 is potassium acetate;

reagent S-2 is selected from tricyclohexylphosphine, 2-di-tert-butylphosphino-3,4,5,6-tetramethyl-2',4',6'-triisopropyl-1,1-biphenyl, 2-(dicyclohexylphosphino)-3,6-dimethoxy-2-4-6-triisopropyl-1,1-biphenyl, triphenylphosphine and 2-dicyclohexylphosphino-2,4,6-triisopropylbiphenyl;

solvent R is selected from tetrahydrofuran, dichloromethane and ethyl acetate;

solvent X is selected from dichloromethane, N,N-dimethylformamide, tetrahydrofuran and ethyl acetate;

solvent Z is selected from tetrahydrofuran/water, methyltetrahydrofuran, dichloromethane and methyltetrahydrofuran/water;

reagent Q is selected from p-toluenesulfonic acid, hydrochloric acid and trifluoroacetic acid;

catalyst U is selected from palladium acetate, (diphenylphosphino)ferrocene dichloropalladium(II), tetrakis(triphenylphosphine)palladium, allylpalladium(II) chloride dimer, di-μ-chlorobis[(1,2,3-η)-1-phenyl-2-propenyl]dipalladium(II) and palladium trifluoroacetate;

base T is selected from sodium carbonate, cesium carbonate and potassium carbonate;

base W is selected from pyridine, triethylamine, diisopropylethylamine and sodium bicarbonate;

base Y is selected from sodium carbonate, diisopropylethylamine, triethylamine, pyridine, sodium bicarbonate, potassium carbonate and sodium hydroxide; and solvent V is selected from dioxane, methylcyclopentyl ether, toluene, methyltetrahydrofuran and tetrahydrofuran.

2. The method as claimed in claim 1, which comprises the following reaction route:

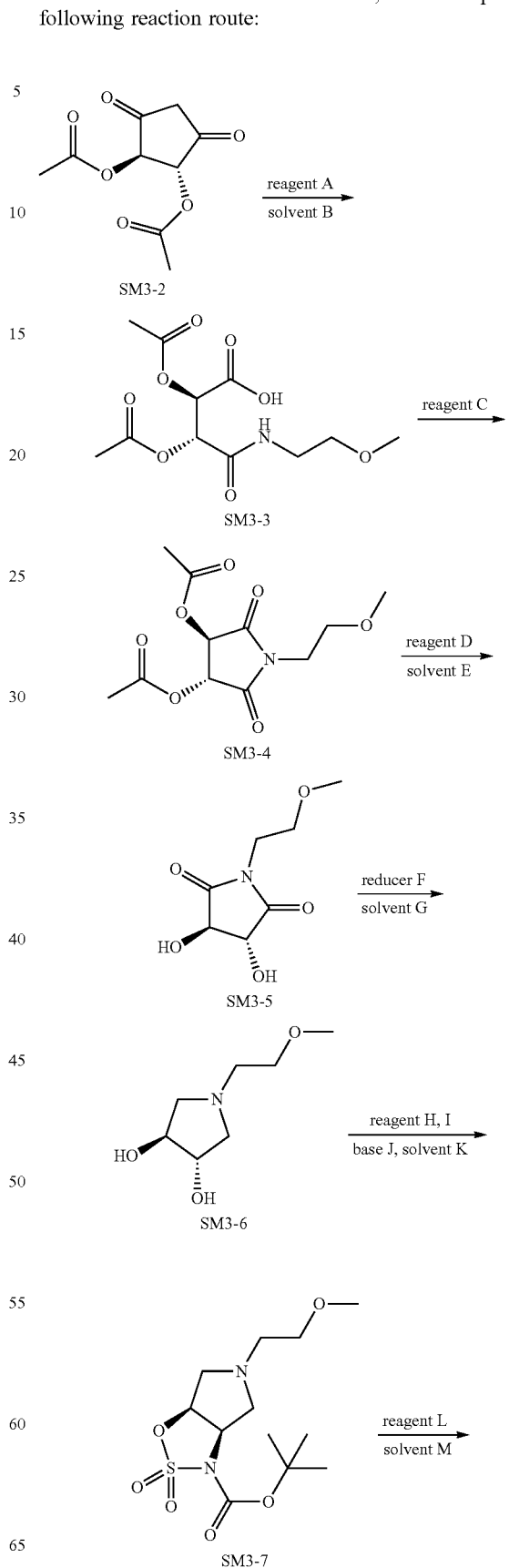

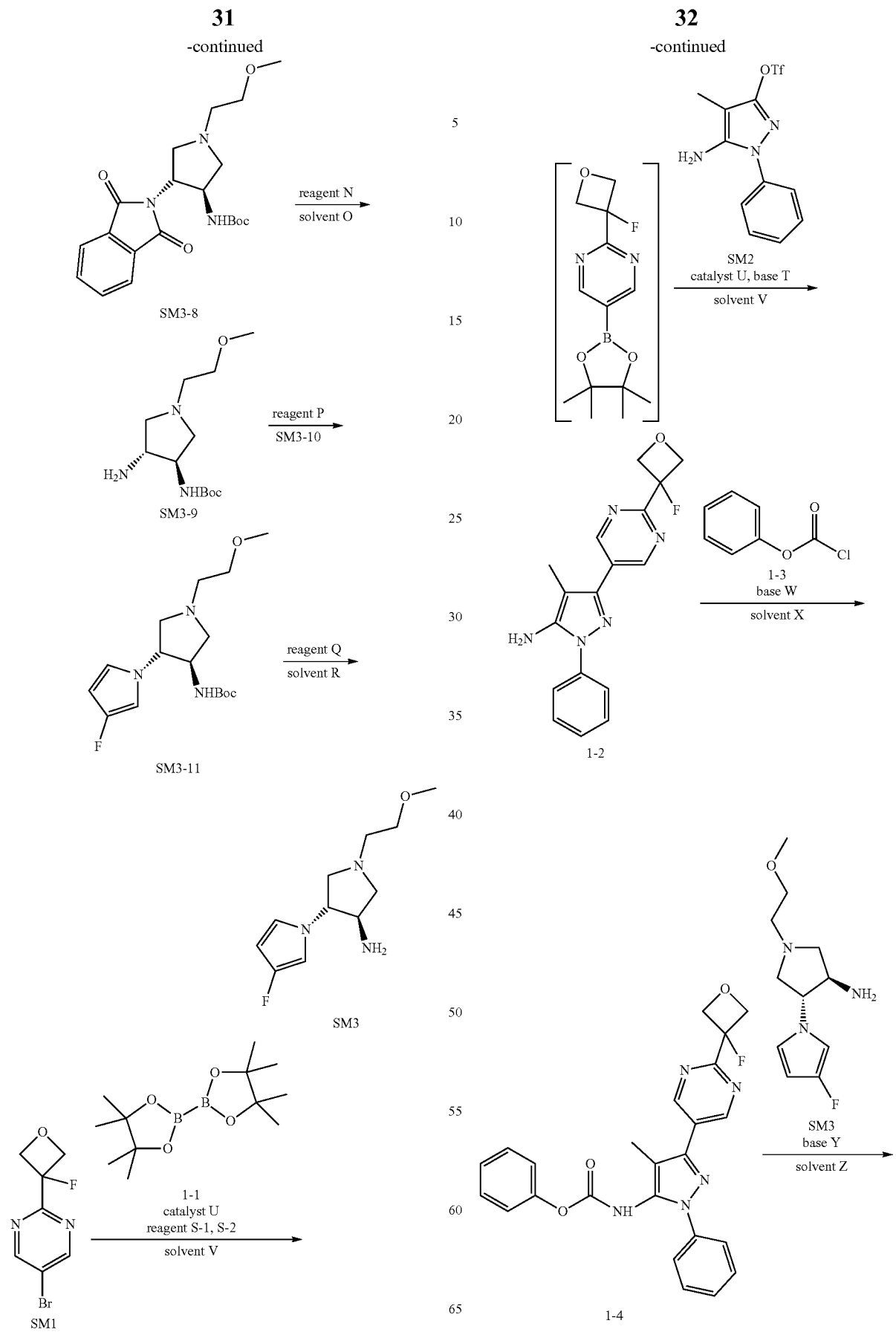

-continued

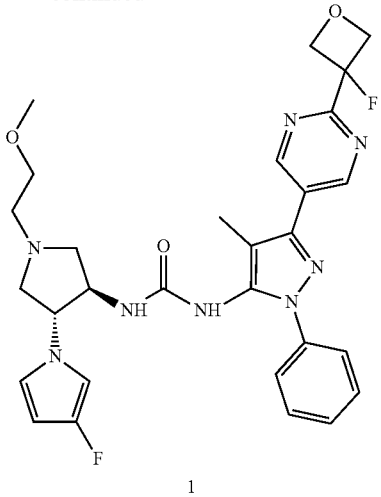

wherein,
reagent A is 2-methoxyethylamine;
solvent B is tetrahydrofuran;
reagent C is acetyl chloride;
reagent D is acetyl chloride;
solvent E is ethanol;
reducing reagent F is selected from lithium aluminum hydride (flake), borane tetrahydrofuran solution and borane dimethyl sulfide complex;
solvent G is tetrahydrofuran;
reagent H is sulfonic acid isocyanate;
reagent I is tert-butanol;
base J is selected from triethylamine and diisopropylethylamine;
solvent K is selected from dioxane and dichloromethane;
reagent L is selected from phthaloyl potassium salt, sodium hydride, potassium tert-butoxide, sodium tert-butoxide, potassium carbonate and 1,8-diazabicyclo[5.4.0]undec-7-ene/phthalamide;
solvent M is selected from NN-dimethylformamide, tetrahydrofuran, methanol, dioxane and dimethyl sulfoxide;
reagent N is hydrazine hydrate; and
solvent O is ethanol.

3. The method as claimed in claim 1, wherein, in the step of preparing compound SM3-11, the temperature range of the reaction system is controlled to be 65±5° C.

4. The method as claimed in claim 1, wherein, the molar ratio of compound SM3-9 to compound SM3-10 is 1:1.2 to 2.

5. The method as claimed in claim 1, wherein, the molar ratio of compound SM1 to catalyst U is 1:0.05 to 0.1.

6. The method as claimed in claim 2, wherein, in the step of preparing compound SM3-3, when adding the materials to the reaction system, the temperature range of the reaction system is controlled to be 0±5° C.

7. The method as claimed in claim 2, wherein, the molar ratio of compound SM3-3 to reagent C is 1:12 to 7.

8. The method as claimed in claim 2, wherein, in the step of preparing compound SM3-5, when adding the materials to the reaction system, the temperature range of the reaction system is controlled to be 0±5° C.

9. The method as claimed in claim 2, wherein, in the step of preparing compound SM3-6, the molar ratio of compound SM3-5 to reducing reagent F is 1:2 to 4.

10. The method as claimed in claim 2, wherein, in the step of preparing compound SM3-7, when adding the materials to the reaction system, the temperature range of the reaction system is controlled to be 15±5° C.

11. The method as claimed in claim 2, wherein, in the step of preparing compound SM3-7, after the reagents addition is complete, the temperature range of the reaction system is controlled to be 20±5° C.

12. The method as claimed in claim 2, wherein, in the step of preparing compound SM3-7, after the completion of the reaction, the reaction system is kept under nitrogen atmosphere for filtration.

13. The method as claimed in claim 2, wherein, in the step of preparing compound SM3-7, after the reagents addition is complete, the temperature range of the reaction system is controlled to be 80±5° C.

14. The method as claimed in claim 2, wherein, in the step of preparing compound SM3-8, the pH is adjusted with acid and controlled at 2.7 to 3.5 in the post-treatment.

15. The method as claimed in claim 2, wherein, in the step of preparing compound SM3-8, the temperature range of the reaction system is controlled to be 35±5° C. when adjusting the pH in post-treatment.

16. The method as claimed in claim 2, wherein, the molar ratio of compound SM3-8 to reagent N is 1:1.5 to 2.

17. The method as claimed in claim 2, wherein, the molar ratio of compound SM3-11 to reagent Q is 1:2.5 to 4.

18. The method as claimed in claim 2, wherein, in the step of preparing compound 1-4, when adding the materials to the reaction system, the temperature range of the reaction system is controlled to be 5±5° C.

19. The method as claimed in claim 2, wherein, in the step of preparing compound 1-4, after the reagent addition is complete, the reaction time is 1.5±0.5 hours.

20. The method as claimed in claim 2, wherein, the molar ratio of compound 1-4 to base Y is 1:5.

\* \* \* \* \*